United States Patent
Carroll

(10) Patent No.: US 7,988,704 B2
(45) Date of Patent: Aug. 2, 2011

(54) SAFE SEPTAL NEEDLE AND METHOD FOR ITS USE

(75) Inventor: Sean M. Carroll, Rancho Cucamonga, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 687 days.

(21) Appl. No.: 12/018,182

(22) Filed: Jan. 22, 2008

(65) Prior Publication Data

US 2008/0125802 A1      May 29, 2008

Related U.S. Application Data

(62) Division of application No. 10/750,097, filed on Dec. 31, 2003, now Pat. No. 7,320,695.

(51) Int. Cl.
    *A61B 17/34*     (2006.01)
(52) U.S. Cl. .................................................... 606/185
(58) Field of Classification Search .................. 606/139, 606/144, 148, 161, 153, 157, 159, 170, 171, 606/174, 185; 604/164.01, 264
See application file for complete search history.

(56) References Cited

U.S. PATENT DOCUMENTS

| | | | |
|---|---|---|---|
| 4,969,875 A | 11/1990 | Ichikawa | |
| 5,334,149 A | 8/1994 | Nortman et al. | |
| 5,476,473 A * | 12/1995 | Heckele | 606/171 |
| 5,928,250 A | 7/1999 | Koike et al. | |
| 6,432,092 B2 | 8/2002 | Miller | |
| 6,540,725 B1 | 4/2003 | Ponzi | |
| 6,575,931 B1 | 6/2003 | Ponzi | |
| 6,595,958 B1 * | 7/2003 | Mickley | 604/164.01 |
| 6,623,473 B1 | 9/2003 | Ponzi | |
| 6,623,474 B1 | 9/2003 | Ponzi | |
| 6,650,923 B1 | 11/2003 | Lesh et al. | |
| 6,656,195 B2 * | 12/2003 | Peters et al. | 606/159 |
| 7,179,256 B2 | 2/2007 | Mest | |
| 7,207,989 B2 | 4/2007 | Pike, Jr. et al. | |
| 7,618,430 B2 | 11/2009 | Scheib | |

OTHER PUBLICATIONS

U.S. Appl. No. 09/711,648, filed on Nov. 13, 2000.

* cited by examiner

*Primary Examiner* — Kevin T Truong
(74) *Attorney, Agent, or Firm* — Christie, Parker & Hale, LLP

(57) ABSTRACT

A method for puncturing a proximal membrane without puncturing a second, distal membrane is provided. The method comprises distally advancing an elongated body through an elongated tubular member to a first position where a distal end of the elongated body is in a first configuration. In the first configuration, the distal end of the elongated body is positioned outside the distal end of the elongated tubular member. The distal end of the elongated body has a distal tip, in this first configuration, that is sufficiently rigid and sharp to puncture the first, proximal membrane. From this first configuration, the distal tip of the elongated body is slightly advanced puncture the first, proximal membrane. After puncturing the first, proximal membrane, the elongated body is advanced through the punctured proximal membrane whereby the distal tip of the elongated body moves into a second configuration. In the second configuration, the distal tip of the elongated body curves into a j-shape, forming a blunt distal surface facing the second, distal membrane.

24 Claims, 8 Drawing Sheets

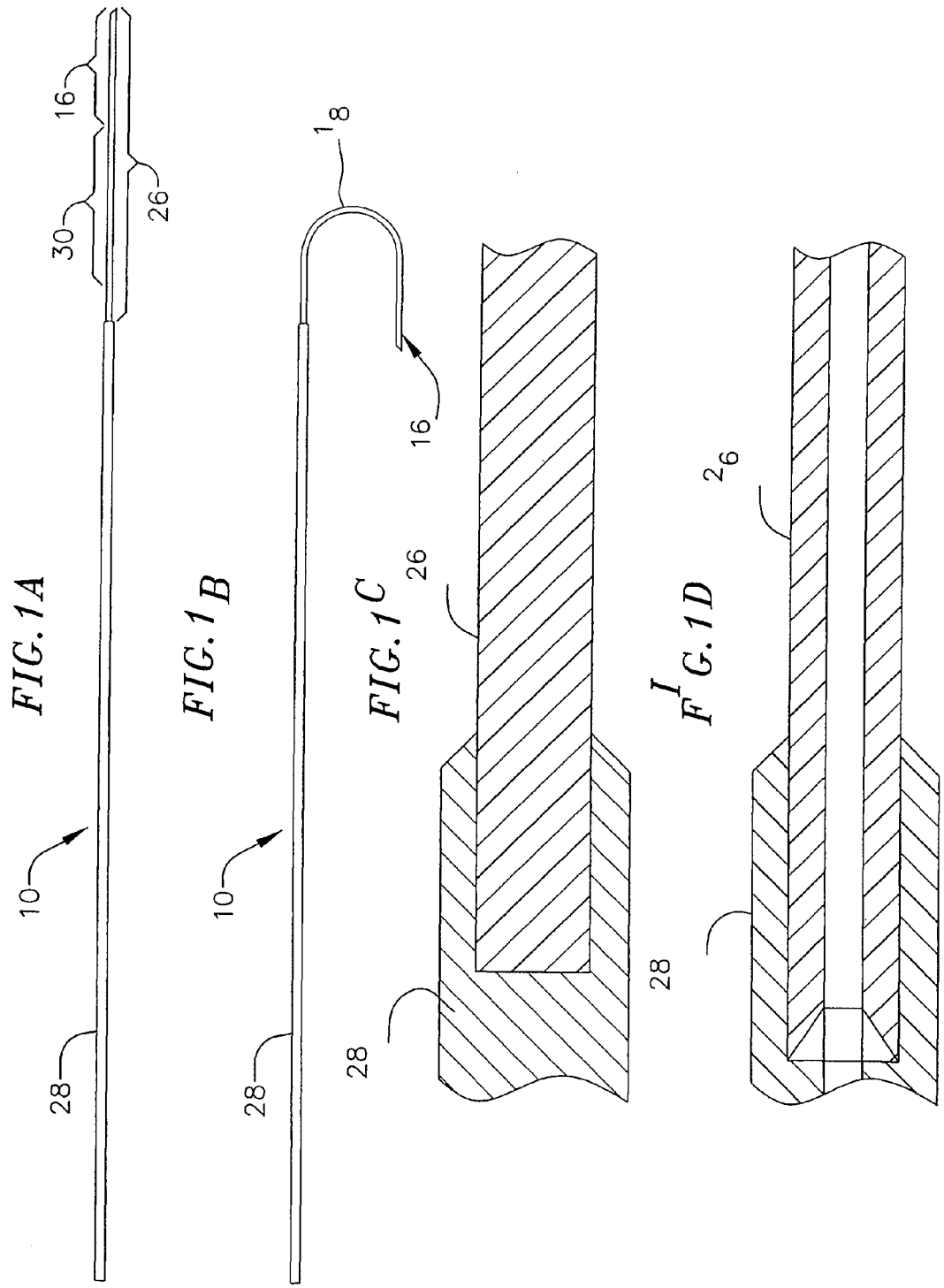

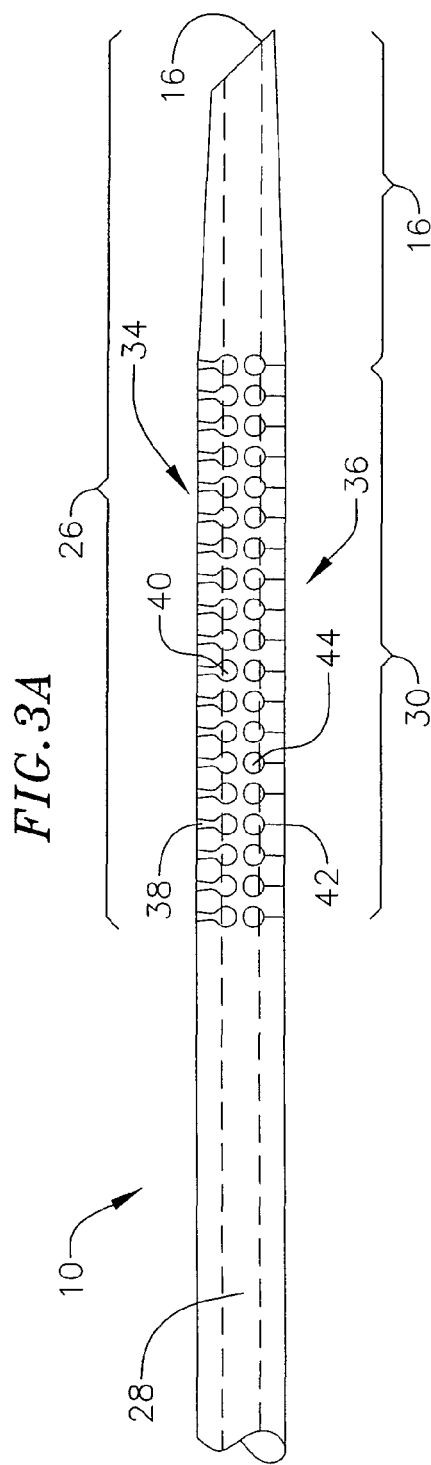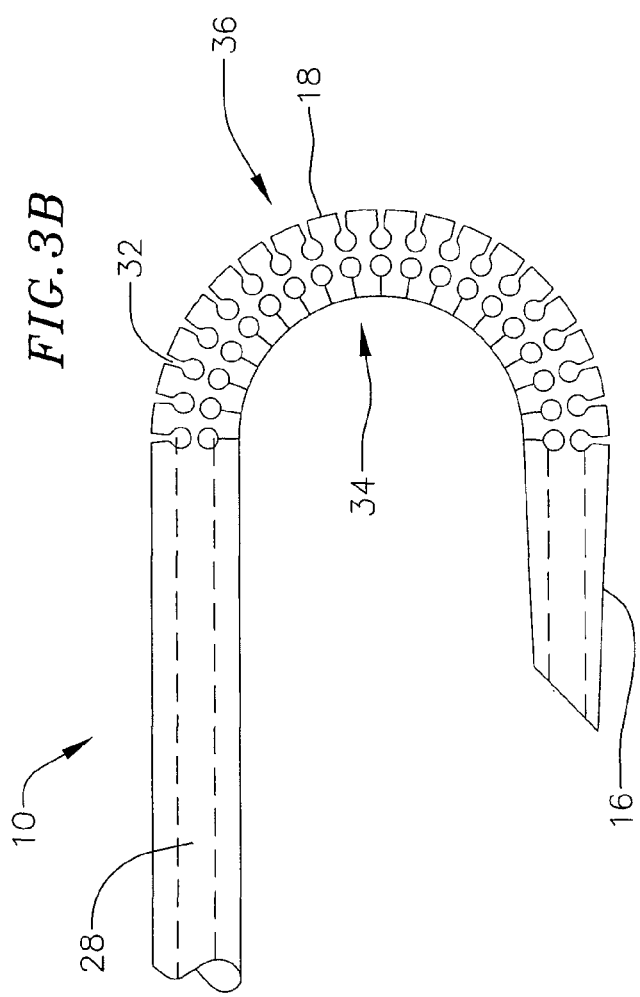

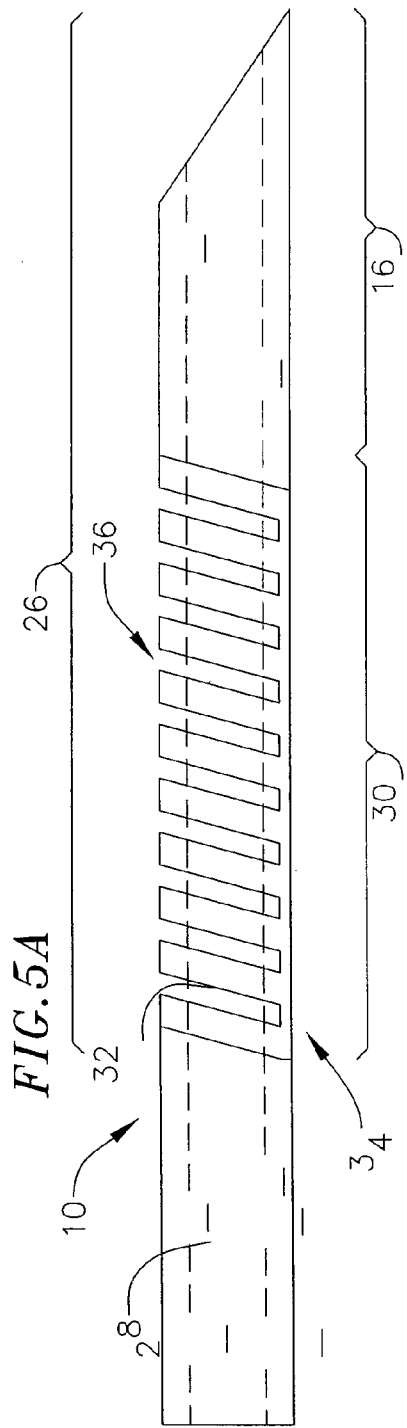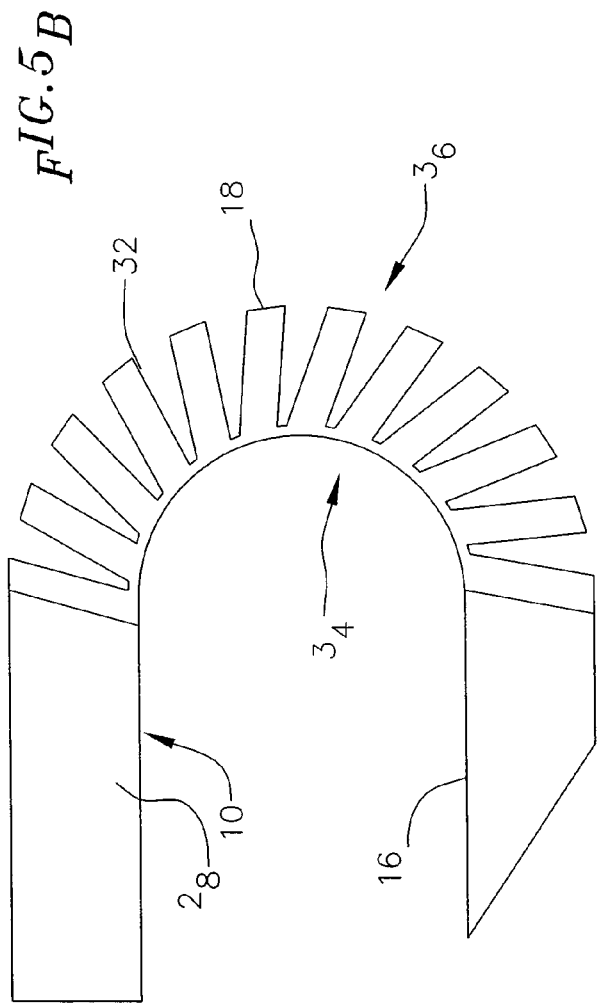

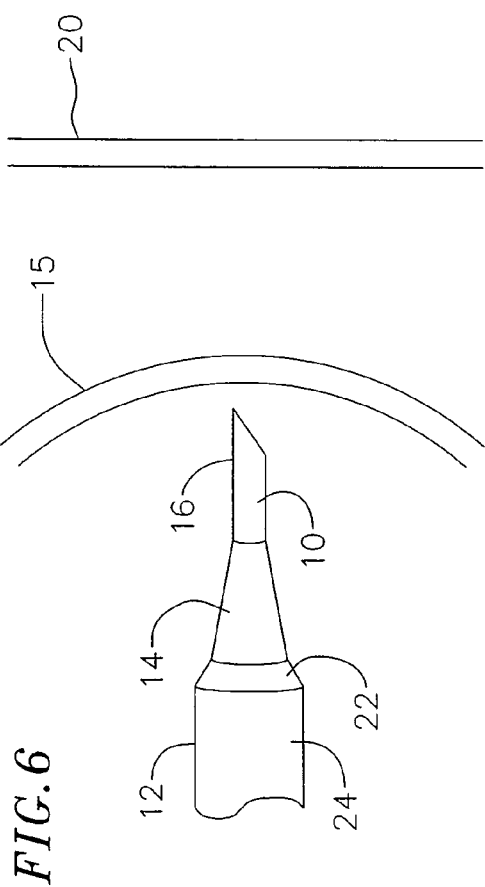
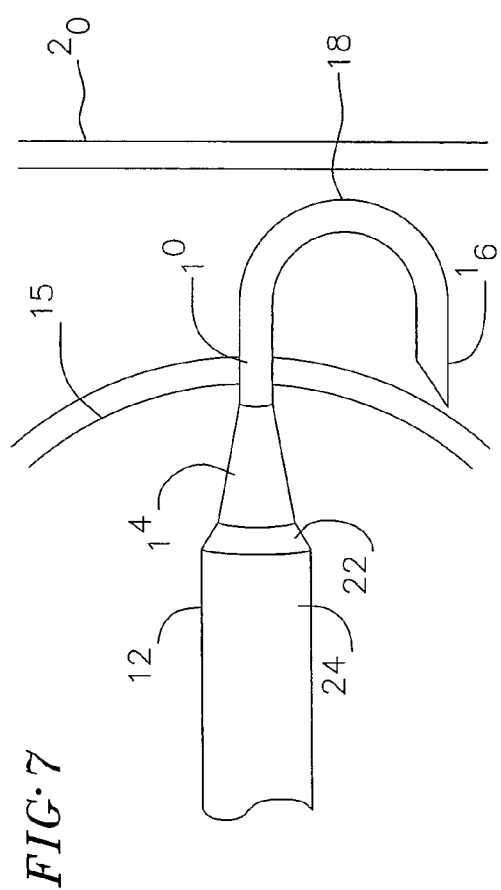
FIG. 6
FIG. 7

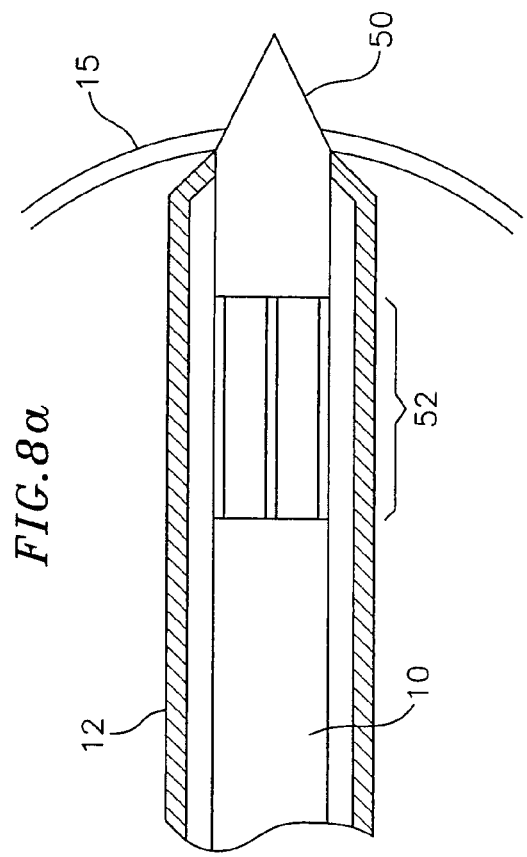
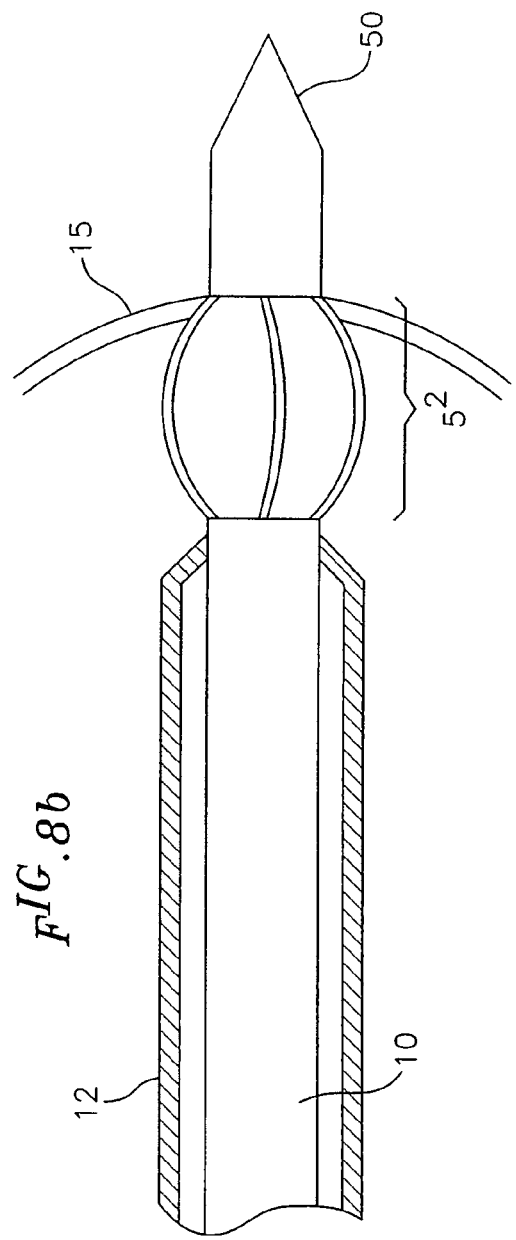

SAFE SEPTAL NEEDLE AND METHOD FOR ITS USE

CROSS-REFERENCE TO RELATED APPLICATION(S)

This application is a divisional of U.S. patent application Ser. No. 10/750,097, entitled SAFE SEPTAL NEEDLE AND METHOD FOR ITS USE, filed Dec. 31, 2003, now U.S. Pat. No. 7,320,695 the entire contents of which is incorporated herein by reference.

FIELD OF THE INVENTION

The present invention is directed to an apparatus and method for introducing an electrophysiology catheter into the left atrium of the heart through the atrial septum and more particularly to an apparatus and method for forming an opening in the atrial septum while minimizing risk of damage to the superior left atrium wall.

BACKGROUND OF THE INVENTION

Electrophysiology catheters are commonly used for mapping electrical activity in a heart. Electrophysiology is a specialty within the field of cardiology for diagnosis and treatment of electrical abnormalities of the heart. By mapping the electrical activity in the heart, ectopic sites of electrical activation or other electrical activation pathways that contribute to heart malfunctions may be detected. This type of information may then allow a cardiologist to intervene and destroy the malfunctioning heart tissues.

Occasionally, an electrical abnormality occurs in a location that is difficult to reach with standard catheter capabilities. The left atrium of the heart is one such location. When an electrical abnormality occurs in the left atrium, a dilation catheter, or dilator, is typically inserted percutaneously, passed through one or more major blood vessels, and inserted into a right atrium of the heart and then passed trans-septally into the left atrium. Specifically, a needle is passed through the dilator and inserted into and through the atrial septum to puncture the atrial septum to allow access to the left atrium for a therapeutic catheter.

A current technique for puncturing the atrial septum includes positioning a dilator adjacent to an area of the atrial septum that is desired to be punctured (typically at the fossa ovalis), inserting a needle into the dilator, feeding the needle through the dilator until the needle protrudes beyond the dilator, and puncturing the atrial septum with the needle. This technique has several disadvantages. For example, locating the desired puncture site and then inserting and feeding a separate needle into the dilator increases the procedure time, and increases the likelihood that the dilator will be inadvertently moved before the needle reaches the desired puncture site, thus requiring a repositioning of the dilator. If the repositioning is performed with the needle inside the dilator, the possibility exists for the needle to slide out of the dilator and damage venous or atrial structures. If the needle is removed during repositioning, procedure time is again extended during reinsertion and re-feeding of the needle into the dilator, and the risk of an inadvertent movement of the dilator during reinsertion and re-feeding of the needle again exists.

Another more serious disadvantage of the current technique is that, to dilate the hole created by the needle puncture sufficiently for a guiding sheath to fit through with the dilator, the sharp needle must be advanced ten to twenty millimeters into the left atrium, which is difficult to control. This advancement brings the sharp edge of the needle dangerously close to the superior wall of the left atrium, and might result in perforation, especially if the left atrium is small. Moreover, a force in an axial direction is required to insert the needle into and through the atrial septum, yet there is no means for controlling the maximum protrusion of the needle from the dilator. As a result, a tendency exists for the operator to continue to apply a forward force to the needle even after the needle has crossed the atrial septum. This risks damage to atrial structures in the left atria or even cardiac puncture if the needle protrudes too far from the dilator.

SUMMARY OF THE INVENTION

The present invention addresses the above-referenced problems by providing a method for puncturing a first, proximal membrane without puncturing a second, distal membrane. This method can be used to puncture the atrial septum without risk of puncturing the lateral left atrial wall. The method comprises providing a device comprising an elongated tubular member and an elongated body slidably disposed within the elongated tubular member. The elongated body has a distal region at least a portion of which is made of a shape-memory material in a preformed curved configuration. The elongated body is movable from a first retracted position completely disposed within the elongated tubular member, which requires the distal tip region of the elongated body to be in a generally straight configuration, to a second extended position where the distal tip region has been advanced out of the distal end of the tubular member. In this extended position, the distal region of the elongated body reverts to its preformed curved configuration.

In the method, the tubular member is advanced in the traditional manner into the right atrium to a position adjacent to a atrial septum. The elongated body is then advanced distally from its first retracted position toward its second extended position. In so doing, the distal end of the elongated body, which has a distal tip portion sufficiently rigid and sharp to puncture the first proximal membrane, e.g., the atrial septum, punctures the first, proximal membrane, e.g., the atrial septum. As the elongated body is further advanced through the punctured proximal membrane, the distal tip of the elongated body deflects into its preformed curved configuration. In the curved configuration, the distal tip of the elongated body is generally hook or j-shaped, creating a "blunt" distal surface that faces the second, distal membrane, e.g., the lateral left atrial wall. As used herein, "blunt" refers to any surface, e.g., a curved surface, that will not puncture the second distal membrane.

BRIEF DESCRIPTION OF THE DRAWINGS

These and other features and advantages of the present invention will be better understood by reference to the following detailed description when considered in conjunction with the accompanying drawings wherein:

FIG. 1a is a side view of the first and second embodiments of the invention in a generally straight configuration;

FIG. 1b is a side view of the embodiments of FIG. 1a in a curved configuration;

FIG. 1c is a side, cross-sectional view of a preferred joint formed between a solid proximal region and a solid distal region of an elongated body as shown in FIG. 1a.

FIG. 1d is a side, cross-sectional view of a preferred joint formed between a tubular proximal region and a tubular distal region of an elongated body as shown in FIG. 1b.

FIG. 2b is a magnified side view of a curved configuration of the distal region of the elongated tube depicted in FIG. 2a;

FIG. 3a is a magnified side view of a generally straight configuration of a key hole cut slotted transformative region of the distal region of an elongated tube;

FIG. 3b is a magnified side view of a curved configuration of the distal region of the elongated tube depicted in FIG. 3a;

FIG. 3c is a perspective view of the transformative region of the embodiment of FIG. 3a.

FIG. 3d is a cut away view of the transformative region of the embodiment of FIG. 3a.

FIG. 5a is a magnified side view of a generally straight configuration of a spiral cut slotted transformative region of the distal region of an elongated tube in which the slots are angled, i.e., not perpendicular to the axis of the transformative region;

FIG. 5b is a magnified side view of a curved configuration of the distal region of the elongated tube depicted in FIG. 5a;

FIG. 6 is a schematic depicting the first configuration of a distal tip of a elongated body according to the invention;

FIG. 7 is a schematic depicting the second configuration of a distal tip of an elongated body according to the invention;

FIG. 8a is a schematic depicting a generally straight configuration of a penetrator mounted on a compression region contained within an elongated tubular member according to an alternative embodiment of the invention;

FIG. 8b is a schematic depicting a generally compressed configuration of the penetrator and compression region depicted in FIG. 8a.

DETAILED DESCRIPTION OF THE INVENTION

Figure 2A:
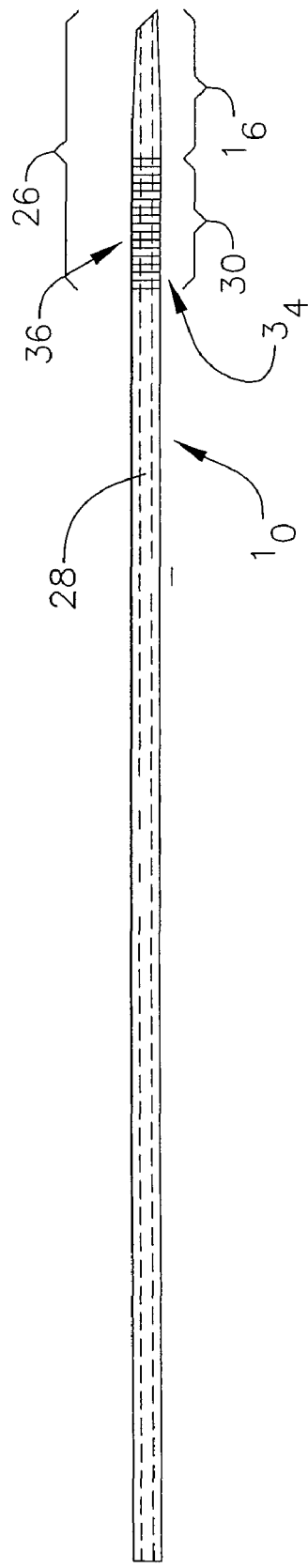
FIG. 2a is a side view of a generally straight configuration of an elongated tube with a box cut slotted transformative region of the distal region.
Figure 2B:
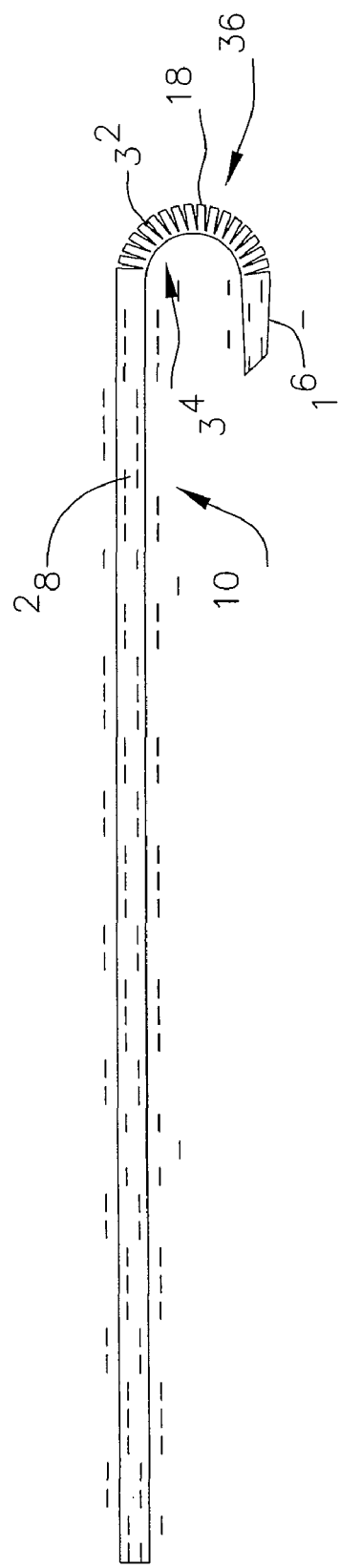
Figure 3C:
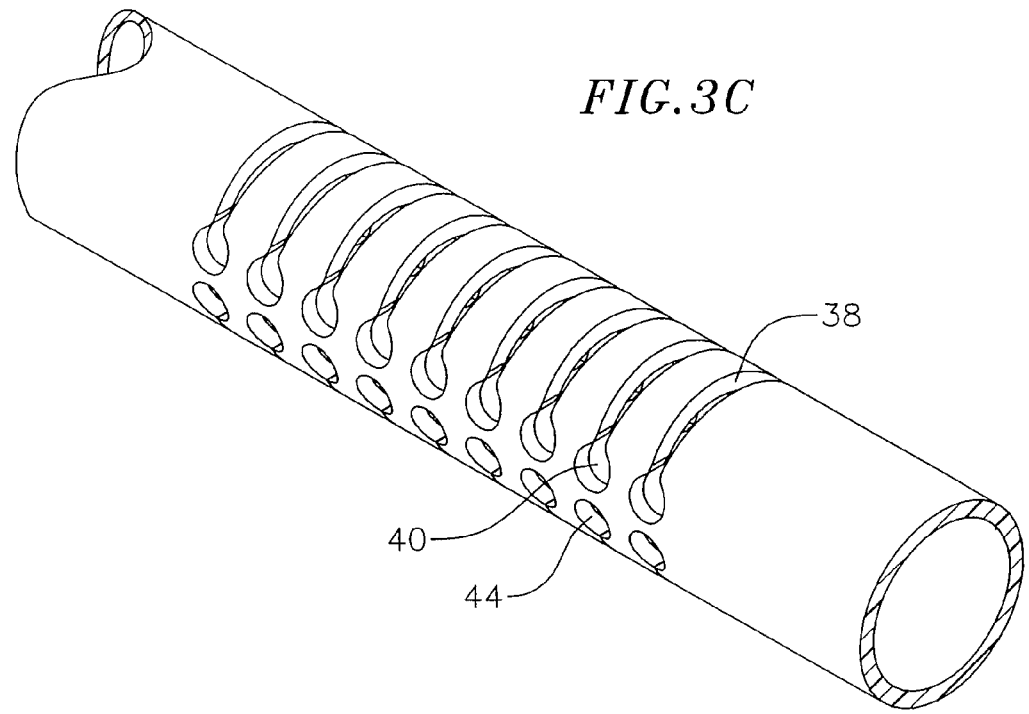
Figure 3D:
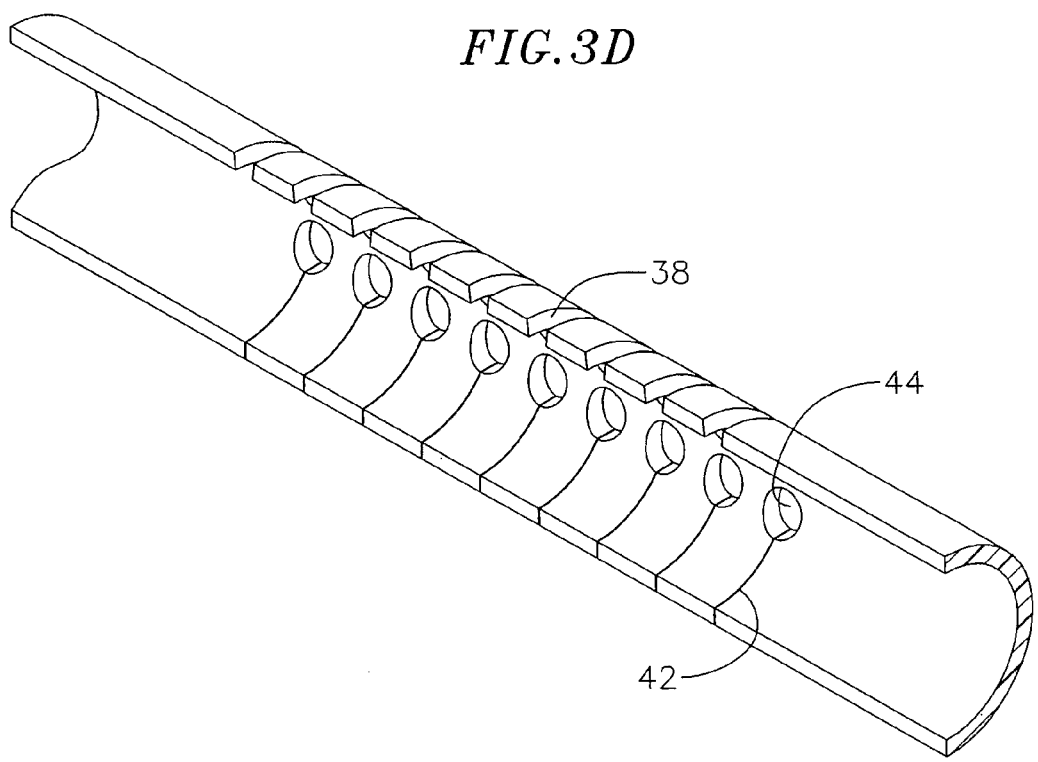

The invention provides a method for puncturing a proximal membrane, e.g., the atrial septum, without puncturing a distal membrane, e.g., the superior left atrium wall. With reference to FIGS. 6 and 7, the method comprises providing a device comprising an elongated body 10 slidably disposed within an elongated tubular member 12. The elongated tubular member 12 may comprise a standard guiding sheath, or a standard vessel dilator. An example of a suitable guiding sheath for use with this invention is the Preface™ Braided Guiding Sheath, commercially available from Biosense Webster (Diamond Bar, Calif.). An example of a suitable dilator for use with this invention is the vessel dilator provided with the Preface™ Braided Guiding Sheath. The elongated tubular member 12 may comprise any suitable material, as is known in the art. Preferably, the elongated tubular member 12 comprises a polymeric construction. The outer diameter of the elongated tubular member 12 preferably ranges from about 6 french to about 12 french. The inner diameter of the elongated tubular member 12 preferably ranges from about 0.018 inch to about 0.040 inch. The distal tip of the elongated tubular member 12 may have an inner diameter ranging from about 0.01 inch to about 0.04 inch. Preferably, the inner diameter at the distal tip ranges from about 0.015 inch to about 0.040 inch.

With reference to FIGS. 1a and 1b, the elongated body 10, comprises a distal region 26, and a proximal region 28. The distal region 26 includes a distal tip portion 16 and a transformative region 30. The distal tip portion 16 of the distal region 26 preferably has a beveled distal end to provide a sharp puncturing tip.

The proximal region 28 comprises an elongated wire or tube made of any suitable material, as is known in the art. Preferably, the proximal region 28 of the elongated body 10 comprises stainless steel or polyamide. The proximal region 28 may comprise a diameter ranging from 0.01 to 0.04 inches. Preferably, the proximal region 28 of the elongated body 10 comprises an outer diameter ranging from 0.015 to 0.035 inches. The distal-most end of the proximal region 28 of the elongated body 10 preferably comprises a circumferential bevel or taper to provide a generally smooth transition between the proximal region and the distal region. The angle of the taper may vary as desired, but should be uniform.

In this embodiment, the distal region 26 of the elongated body 10 may be solid or tubular. At least the transformative region 30, and preferably the entire distal region 26, is made of a shape-memory material. As used herein "shape-memory" refers to the property of certain materials that allows the material to return to its preformed shape after being bent as a result of an applied force. Any suitable shape-memory material may be used. Preferably, the distal region 26 of the body 10 is made of nitinol or shape memory polymer. The distal region 26 of the elongated body 10, if solid, preferably has a diameter ranging from about 0.010 inch to about 0.035 inch, and more preferably about 0.015 inch. If tubular, the outer diameter ranges from about 0.010 inch to about 0.035 inch, and the inner diameter ranges from about 0.007 inch to about 0.032 inch. More preferably, the outer diameter is about 0.015 inch and the inner diameter is about 0.012 inch:

The distal tip portion 16 of the elongated wire or tube 10 is of sufficient length to puncture completely through the proximal membrane 15, e.g., the atrial septum. In a preferred embodiment, the length of the distal tip 16 ranges from about 0.10 inch to about 0.30 inch. Preferably, the length of the distal tip portion 16 ranges from 0.120 to 0.170 inches.

The proximal region 28 and the distal region 26 of the elongated body 10 may all comprise a single unitary structure or may be separate structures which are joined. If a single connecting wire or tube is used, it should have shape-memory capability. If the proximal and distal regions 28 and 26 are separate structures, they may be joined by way of suitable means. For example, as shown in FIGS. 1c and 1d, the proximal region 28 may have an axial recess—at its distal end which recesses the proximal end of the wire or tube that forms the distal region 26. This joint may be secured by welding, adhesive, or any other suitable means.

The distal region 26 of the elongated body 10 includes a transformative region 30, located immediately proximal to the distal tip portion 16 of the elongated body 10 that is preformed into a curved configuration. When the transformative region 30 is confined within the elongated tubular member 12, with the distal end of the distal tip portion 16 outside the distal end 14 of the elongated tubular member 12, the transformative region 30 is maintained in a generally straight configuration. The distal tip portion 16, which is generally rigid and sharp punctures the proximal membrane 15 upon distal advancement out of the tubular member 12 against the proximal membrane 15. As the transformative region 30 is advanced distally out of the distal end 14 of the elongated tubular member 12 to its extended position, it returns to its preformed, e.g., curved shape, as shown in FIG. 7, thus providing a curved or blunt distal surface 18 facing the distal membrane 20.

In a preferred embodiment, the distal region 26 has a length ranging from about 0.1 inch to about 0.3 inch. More preferably, the length of the distal region 26 ranges from about 0.165 inch to about 0.255 inch. The preferred range allows the distal tip portion 16, in a sufficiently straight configuration, to penetrate the first membrane and thereafter bend in a sufficiently small radius to ensure that the tip turns prior to engaging the second membrane. The transformative region 30 may be curved at any radius suitable to create a blunt distal surface 18 facing the distal membrane 20. When the elongated body 10 comprises an elongated tube, it may be used to deliver fluid, such as contrast media, saline and/or drugs to the region of the punctured proximal membrane 15, as discussed further below.

In other embodiments, depicted in FIGS. 2a, 2b, 3a, 3b, 3c, 3d, 5a, and 5b, the elongated body 10 comprises an elongated tube having a "slotted" transformative region 30 and a rigid, non-slotted, distal tip portion 16 of sufficient length to puncture entirely through the proximal membrane 15. At least the slotted transformative region 30 and preferably the entire distal region 26 is made of a shape-memory material, e.g., nitinol. The transformative region 30 comprises a plurality of slots or shaped cuts (collectively referred to herein as "slots") to promote flexibility and to enable a tighter bending radius, to thereby provide a curved, non-puncturing surface 18 facing the distal membrane 20 once the proximal membrane has been punctured. In such embodiments, the transformative region 30, which is preformed into a curved configuration will regain that precurved configuration upon advancement out of the tubular member 12 and through the punctured proximal membrane 15.

The slotted transformative region 30 also serves to control the direction and extent of bending of the distal end 26 of the elongated tube 10. That is, the slotted transformative region 30 may include one or more partial circumferential slots 32 extending through the outer wall of the elongated tube which affect the direction in which and the extent to which the transformative region 30 can bend. The slots 32 of the slotted transformative region 30 may be arranged to permit the distal region 26 of the elongated tube 10 to bend in only one direction, as shown. In such an arrangement, the slots 32 may be aligned along the axis of the slotted transformative region 30. Alternatively, the slots 32 of the slotted transformative region 30 may be arranged such that the distal region 26 of the elongated tube 10 bends in more than one plane, e.g., the slots are not axially aligned.

With particular reference to FIGS. 3a-d, the outer wall of the slotted transformative region 30 can be viewed as having a first, preferably compressible, side 34 and a second, preferably expandable, side 36 opposite the first side. The first side 34 is the side forming the inner radius of the curve formed by the transformative region 30 once extended out of the tubular member 12. The second side 36 is the side forming the outer radius of the curved transformative region 30.

The slotted transformative region 30 includes a plurality of slots 32 that extend from the second side 36 toward the first side 34 and/or a plurality of slots that extend from the first side 34 toward the second side 36. The number, size, geometry and location of the slots may vary as desired. Preferably the slots are uniformly spaced, but the spacing may vary as desired in order to achieve the desired geometry.

In the embodiment shown in FIG. 2a, each slot 32 may be generally perpendicular to the long axis of the transformative region 30. Alternatively, as depicted in FIG. 5a, the slots 32 could be angled relative to the axis of the transformative region 30, so long as the slots 32 are generally transverse to the long axis of the transformative region 30.

In the embodiment shown in FIGS. 3a-d, both the first side 34 and the second side 36 include a plurality of slots 32. The slots extending from the first side 34 toward the second side 36 are preferably aligned with the slots extending from the second side 36 toward the first side 34 as shown. Also, as shown, the width of the slots extending from the first side 34 toward the second side is sufficient to allow the transformative region to bend to the desired curvature.

In this arrangement, when the transformative region returns to its preformed curved configuration, the walls of the slots in the first side 34 compress toward each other and the walls of the slots in the second side 36 expand away from each other as shown in FIG. 3b. The number, placement, size and shape of the slots can vary depending on the desired effect. Preferably, the total number of slots in the slotted transformative region 30 ranges from about 30 to about 200, and the center of the slots are spaced apart by a distance of from about 0.008 inch to about 0.180 inch, preferably about 0.060 inch.

The "depth" of the slots 32, i.e., the circumferential arc in the wall of the tubular shaft of the tip region 26 made by the slots may also vary. In the embodiment shown in FIGS. 3a and 3b, the circumferential arc of the slots 32 does not extend past the longitudinal midline of the transformative region 30. In other embodiments where the slots in the first side 34 are not aligned with the expandable slots in the second side, the slots may, if desired, extend past the longitudinal midline of the transformative region. The arcs of the compressible slots may vary from each other and may vary from those of any expandable slots.

The shapes and placement of the slots can affect the extent to which, and the direction in which, the slotted transformative region 30 will bend. In the embodiment depicted in FIGS. 3a-d, the slots are generally "key-hole" shaped when viewed from the side. Specifically, each compressible slot comprises a rectangular or preferably slightly tapered or trapezoidal region 38 that terminates in a general circular region 40. Thus, the compressible slots of this embodiment, as well as that of FIGS. 4 and 5, involve the removal of material from the transformative region 30.

In the embodiment of FIGS. 3a-3d, each expandable slot comprises a cut 42 generally perpendicular to the axis of the transformative region 30. The cuts 42 terminate in generally circular regions 44 like the circular regions 40 of the compressible slots. The circular regions 44 of the expandable slots can have the same size as those of the compressible slots or may differ as desired. It is understood that the walls formed by cuts 42 may be spaced apart if desired.

Figure 4A:
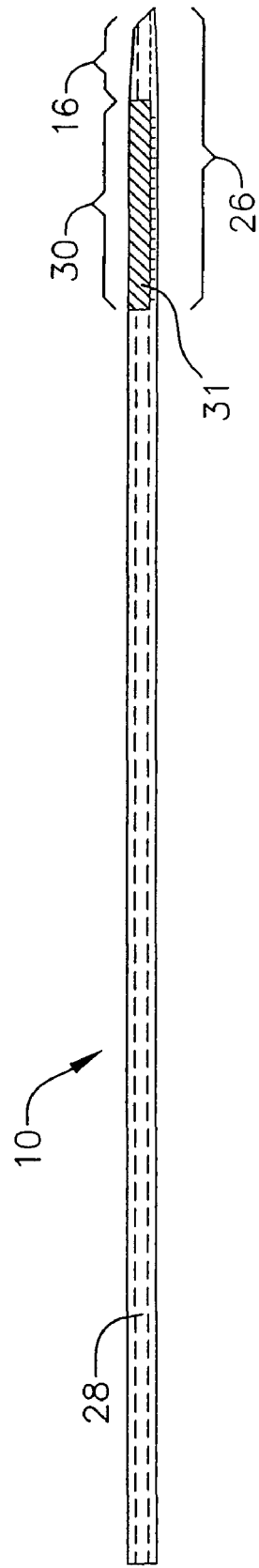
FIG. 4a is a side view of another embodiment of the invention in a generally straight configuration in which a portion of the transformative region has been removed.
Figure 4B:
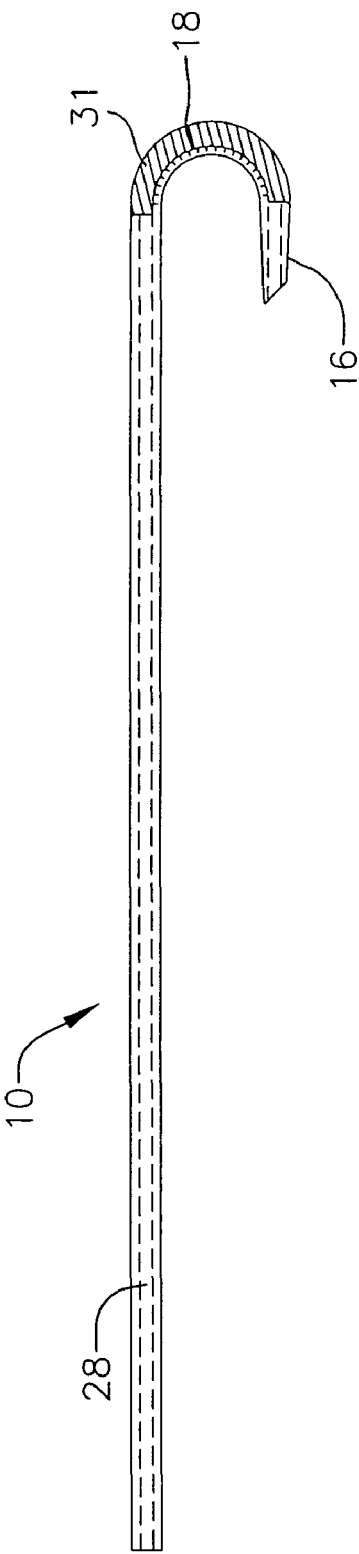
FIG. 4b is a side view of the embodiment of FIG. 4a in a curved configuration.

In another embodiment, the elongated body 10 comprises an elongated tube, as described above, wherein a substantial portion of the transformative region 30 of the elongated body 10 is completely removed, as depicted in FIGS. 4a and 4b. Removal of a substantial portion of the transformative region 30 helps promote flexibility of that region enabling a tighter bending radius and reducing strain on the tubing which increases the ability of the assembly to withstand fatigue. The transformative region 30 may be pre-curved in any radius suitable to present a non-puncturing surface 18 toward the distal membrane 20. Preferably, the transformative region 30 has a preformed curvature from about 120° to about 270°, preferably 180°, and has a radius of about 0.160 inch to about 0.300 inch, preferably about 0.250 inch.

In any of the embodiments where a portion of the transformative region 30 is removed, a polymeric covering 31 may optionally be coated onto the transformative region 30 to cover any sharp edges. If desired, the polymeric coating 31 may be coated over the entire length of the elongated body 10. The polymeric covering 31 may comprise any suitable material, as is known in the art, e.g., nylon, polyurethane, fiberglass reinforced plastic, or polyester. Preferably, the polymeric covering 31 comprises a highly flexible segment that acts as a fluid conduit to the distal tip portion 16. For example, the polymeric covering 31 may comprise a permeable or semi-permeable membrane for delivering fluids, such as contrast media, saline or drugs.

In those embodiments having a slotted transformative region 30 when the elongated body 10 is advanced distally such that the distal region 26 extends out of the tubular member 12, the slotted transformative region 30 will bend in a direction toward the compressible side 34 and return to its preformed curved configuration. Each of the above-described arrangements of the slots 32 enables the transformative region 30 to bend generally within a single desired plane, assuring that the distal region 26 bends in a manner to carry the sharp distal tip portion 16 away from the second or distal membrane.

In an alternative embodiment, depicted in FIGS. 8a and b, the elongated body 10 comprises a penetrator 50 mounted on a compression region 52. The penetrator is sufficiently long to puncture entirely through the proximal membrane 15, and comprises any suitable, generally non-compressible material. The compression region 52 may either comprise a very flexible tubular material, e.g., a flexible polymer, or a plurality of strips of a flexible material attaching the penetrator to the elongated body 10.

In these embodiments, the compression region 52 remains in a generally straight and rigid configuration while contained within the elongated tubular member 12, as shown in FIG. 8a. While the compression region 52 is so contained, the penetrator 50 punctures completely through the proximal membrane 15. Upon advancement out of the elongated tubular member 12, the compression region 52 compress and/or flexes, e.g. bows outwardly, upon terminating the advancement of the penetrator, as shown in FIG. 8b. The compression of the compression region 52 prevents the penetrator from puncturing a second membrane by eliminating the support behind the penetrator that is needed to force the penetrator through the membrane. Any material may be used for the compression region 52 that is sufficiently flexible such that the compression region 52, when advanced out of the elongated tubular member 12, will compress upon contact of the penetrator with a second membrane.

Each embodiment of the present invention may further comprise a handle shaped to allow precise manipulation of the elongated body 10 and the elongated tubular member 12. The handle controls the direction of curvature of the elongated body 10, as well as both the advancement of the elongated body 10 and the advancement of the elongated tubular member 12. Also, the handle facilitates the separate advancement of the elongated body 10 relative to the advancement of the elongated tubular member 12.

The handle may also optionally include either a pressure transducer or a connection to a pressure transducer for monitoring the pressure surrounding the elongated body 10. In those embodiments where the elongated body 10 comprises an elongated tube, the handle may also include a standard luer lock connection to facilitate infusion of fluids through the elongated tubular body 10. Nonlimiting examples of handles suitable for use with the present invention include those disclosed in U.S. Pat. Nos. 6,540,725, 6,575,931, 6,623,473 and 6,623,474, and U.S. patent application Ser. Nos. 10/118,679, 10/693,553, 10/694,118, 09/711,648, the entire disclosures of which are incorporated herein by reference.

Each embodiment of the present invention may be used to puncture the atrial septum of the heart, and thereby gain access to the left atrium of the heart. In this trans-septal puncture procedure, the atrial septum is the proximal membrane 15 to be punctured, and the lateral left atrial wall is the distal membrane 20 not to be punctured. To puncture the atrial septum, the distal region of the elongated tubular body 10 is positioned against the atrial septum, typically at or near the fossa ovalis. The elongated body 10 is then distally advanced through the elongated tubular member 12 to the first configuration, depicted in FIG. 6, to its extended position outside the distal end 22 of the elongated tubular member 12. The distal tip portion 16 of the elongated body 10 is sufficiently rigid and sharp to puncture the atrial septum. As the distal region 26 of the elongated body 10 is advanced through the elongated tubular member 12, it returns to its preformed curved configuration, depicted in FIG. 7. In the curved configuration, the distal tip portion 16 of the elongated body 10 points away from the lateral left atrial wall, thereby preventing the puncture of the lateral left atrial wall.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention.

For example, where the elongated body 10 is an elongated tube, fluid, such as contrast media, saline or drugs such as anticoagulants, can be delivered across the atrial septum into the left atrium of the heart. Contrast media is useful for determining the position within the heart where the elongated tubular member and the elongated body are located. Drugs, such as anticoagulants, can be used to control the clotting of blood at the puncture site.

As another example, the elongated body 10 can have a pressure monitoring device, if desired, mounted on its proximal end. Such a pressure monitoring device can be used to determine the location of the elongated body 10 within the heart due to the differences in pressure among the different chambers within the heart. For example, the pressure within the right atrium of the heart differs from that of the left atrium and from aortic pressure or pressure within a pulmonary artery. A pressure monitoring device will read the pressure at the location of the elongated body, and that reading will indicate whether the elongated body is located within the right atrium, the left atrium, a pulmonary artery or the aorta.

Accordingly, the foregoing description should not be read as pertaining only to the precise structures described and shown in the accompanying drawings, but rather should be read as consistent with and as support for the following claims, which are to have their fullest and fairest scope.

What is claimed is:

1. A device for puncturing a proximal membrane without puncturing a distal membrane comprising:
    a first elongated tubular member comprising proximal and distal ends and at least one lumen therethrough;
    a second elongated tubular member having proximal and distal ends and being slidably disposed within the lumen of the first elongated tubular member, wherein the distal end of the second elongated tubular member has a distal tip sufficiently sharp to puncture the proximal membrane, the distal tip having a first configuration when constrained by the first elongated tubular member, configured to puncture the proximal membrane, and wherein the distal tip of said second elongated tubular member automatically transitions to a second configuration that is incapable of puncturing the distal membrane upon exiting the distal tip of the first elongated tubular member.

2. A device according to claim 1, further comprising a third tubular member encasing the first elongated tubular member.

3. A device according to claim 2, wherein the first elongated tubular member is a vessel dilator.

4. A device according to claim 1 wherein the second elongated tubular member includes a shape memory component.

5. A device according to claim 1, wherein the distal tip of the second elongated tubular member is spiral cut such that the distal tip automatically becomes highly flexible after puncturing the proximal membrane.

6. A device according to claim 1, wherein the distal tip of the second elongated tubular member is otherwise cut such that the distal tip automatically becomes highly flexible after puncturing the proximal membrane.

7. A device for puncturing a proximal membrane without puncturing a distal membrane comprising:
   a first elongated tubular member comprising proximal and distal ends and at least one lumen therethrough;
   a second elongated member having proximal and distal ends and being slidably disposed within the lumen of the first elongated tubular member, wherein the distal end of the second elongated member has a distal tip sufficiently sharp to puncture the proximal membrane, the distal tip having a first configuration when constrained by the first elongated tubular member, configured to puncture the proximal membrane, and wherein the distal tip of said second elongated member automatically transitions to a second configuration that is incapable of puncturing the distal membrane upon exiting the distal tip of the first elongated tubular member.

8. A device according to claim 7, further comprising a third tubular member encasing the first elongated tubular member.

9. A device according to claim 8, wherein the first elongated tubular member is a vessel dilator.

10. A device according to claim 7 wherein the second elongated tubular member includes a shape memory component.

11. A device according to claim 7, wherein the distal tip of the second elongated member is wound in a spiral.

12. A device according to claim 7, wherein the distal tip of the second elongated member is bent in a curve.

13. A device for puncturing a proximal membrane without puncturing a distal membrane comprising:
   a first elongated tubular member comprising proximal and distal ends and at least one lumen therethrough;
   a second elongated tubular member having proximal and distal ends and being slidably disposed within the lumen of the first elongated tubular member, wherein the distal end of the second elongated tubular member has a distal tip sufficiently sharp to puncture the proximal membrane, the distal tip having a first configuration outside a distal end of the first elongated tubular member configured to puncture the proximal membrane, and wherein the distal tip automatically moves to a second configuration having a blunt distal surface facing the distal membrane after puncturing the proximal membrane.

14. A device according to claim 13, further comprising a third tubular member encasing the first elongated tubular member.

15. A device according to claim 14, wherein the first elongated tubular member is a dilator.

16. A device according to claim 13 wherein the second elongated tubular member comprises nitinol.

17. A device according to claim 13, wherein the distal tip of the second elongated tubular member is spiral cut such that the distal tip automatically becomes floppy after puncturing the proximal membrane.

18. A device according to claim 13, wherein the distal tip of the second elongated tubular member is box cut such that the distal tip automatically becomes floppy after puncturing the proximal membrane.

19. A device for puncturing a proximal membrane without puncturing a distal membrane comprising:
   a first elongated tubular member comprising proximal and distal ends and at least one lumen therethrough;
   a second elongated tubular member having proximal and distal ends and being slidably disposed within the lumen of the first elongated tubular member, wherein the distal end of the second elongated tubular member has a distal tip sufficiently sharp to puncture the proximal membrane, the distal tip having a first configuration outside a distal end of the first elongated tubular member configured to puncture the proximal membrane, and wherein the distal tip is cut such that the distal tip automatically becomes floppy after puncturing the proximal membrane to thereby prevent puncturing the distal membrane.

20. A device according to claim 19, further comprising a third tubular member encasing the first elongated tubular member.

21. A device according to claim 20, wherein the first elongated tubular member is a dilator.

22. A device according to claim 19 wherein the second elongated tubular member comprises nitinol.

23. A device according to claim 19 wherein the distal tip is spiral cut.

24. A device according to claim 19, wherein the distal tip is box cut.

* * * * *